United States Patent [19]

Austin

[11] Patent Number: Plant 7,564

[45] Date of Patent: Jun. 25, 1991

[54] ROSE PLANT— AUSWHITE

[75] Inventor: David C. H. Austin, Albrighton, England

[73] Assignee: David Austin Roses, Albrighton, England

[21] Appl. No.: 435,076

[22] Filed: Nov. 9, 1989

[51] Int. Cl.[5] ..... A01H 5/00

[52] U.S. Cl. ..... Plt./1

[58] Field of Search ..... Plt. 1

*Primary Examiner*—James R. Feyrer

*Attorney, Agent, or Firm*—Ladas & Parry

[57] ABSTRACT

A new variety of rose plant of the shrub class distinctive in its character by its fully double flowers of yellowish white with abundant, continual blooming and the unusual blend of colouring and shaping of the flower.

1 Drawing Sheet

BACKGROUND OF THE INVENTION

The present invention relates to a new and distinct variety of shrub rose, seedling resulting from a definite effort to produce an improvement in this class of roses.

BRIEF SUMMARY OF THE INVENTION

Primary features of this new variety which connote a distinctive advance over existing types are the gross abundant and continual blooming taken with the perfection of the fully double flowers of an old-fashioned, more particularly apparent in the accompanying illustration of a specimen thereof.

BRIEF DESCRIPTION OF THE DRAWING

The drawing is a colour photographic representation of a new variety of flush of bloom taken substantially in side view and showing inflorescence in various stages, stems and foliage of the plant.

DETAILED BOTANICAL DESCRIPTION

The following is a detailed description of the new variety, colour terminology being in accordance with the "Methuen Handbook of Colour" published by Eyre Methuen Ltd (1963).

Variety denomination (in accordance with the UPOV Convention): Auswhite (Trade name The Swan).

Type: Hardy: bush; outdoor; seedling; for cut flowers and garden decoration.

Class: Shrub.

Propagation: Holds its distinguishing characteristics through succeeding propagations by budding.

The rose plant was grown at Albrighton, Nr. Wolverhampton, England and was derived as follows:

Female parent (Seed parent): Charles Austin.

Male parent (Pollen parent): Seedling × Iceberg.

The operation of the artificial pollination is therefore expressed by the following (Charles Austin × seedling × Iceberg).

The following observations are made of specimens grown outdoors in England.

Plant description:

*Plant.*—Height — 140 cm. Habit — Tall, strong, upright.

Branches:

*Young stems.*—Colour: Lettuce green 30D7 with red 9D8 shading on underside. Texture: Glabrous, smooth, semi-shiny. Thorns: Very occasional.

*Old stems.*—Colour: Greenish white with pink tinge 30E8 Parrot green. Texture: glabrous, smooth, semi-shiny. Thorns: Occasional, 0–3 per node. Brownish red 10C7 fading to light yellow 4A4.

Leaves:

*Stipules.*—Length av. 25 mm. Width 4–6 mm. Angle of wingtips to petiole: 80 slightly recurved towards stem. Margins: Minutely serrate with glandular hairs. Shape: Linear. Colour: 29D7 greyish green fading to 1B4 greyish yellow midline.

Petiole:

*General description.*—Densely tometose when young, glabrous when old.

*Groove/hairs/thorns.*—Groove lined with red 10C8 tipped glandular hairs.

*Young petiole.*—Densely tometose.

*Old petiole.*—Glabrous.

*Upperside color.*—29E8 deep green.

*Underside color.*—29C6 greyish green.

*Hair/thorns.*—Occasional red 10C7 tip hairs. Occasional pale/yellow/green thorns with brownish red tinge 7D8.

*Leaflets.*—Number: 3, 5 most often. 7. Shape: Oval with rounded base, cuspidate apex. Serration: Regularly serrate. Texture: Leathery.

General effect of foliage: Medium density, semi-glossy.

Colour:

*Young foliage.*—30E7 grass green with reddish brown 8D7 veins. Upperside: Capillaries and margin. Underside: 30D6 leaf green with reddish brown 8D8 veins, particularly pronounced towards margins.

*Adult foliage.*—Upperside: 28F 6/7 dark green. Underside: 29E 5/6 greyish green.

Inflorescence:

*Number of flowers per stem.*—1–6, mainly 3.

*Peduncle.*—Length: Very variable 20–60 mm. Colour: 29D 6/7 greyish green. Thorns/hairs: red 10C8 tipped glandular hairs — medium density.

*Sepals.*—Upperside colour: Greyish green 29D8 with red blush 10A4 midline base and margins Outer margins: Ensiform protrusions and red 9B7 glandular hairs. Inner margins: Tomentose. Underside colour: 29C7 apple green. Texture: Inside, densely tometose. Sepal length: 25–30 mm. Bud shape: Oval. Long pointed apex. Bud length: 30–40 mm. Max. width: 15–18 mm before bud break. Colour when opening: Pale yellow/-cream 4A3. Strew yellow 3B4 at base. Flower shape: As a flattened cap, rounded base, flattened top. Outer petals recurved towards the stem in mature flowers. Diameter: 75–100 mm.

Flower colour when blooming:

*Outer petals.*—Yellowish white 1A2, yellow 2A6 at base.

*Upperside.*—Inner petals — pale yellow 2A3, deepening to pastel yellow 3A4 and light yellow 3A5.

*Outer petals.*—Yellowish white 1A2.

Flower colour when opening:

*Upperside.*—Pale yellowish white 2A2 deepening towards centre and base of petal to pale yellow 2A3.

*Underside.*—1A2 yellowish white 2A2 deepening to pale yellow 2A3 at base.

Flower colouring when finished blooming:

*Upperside.*—Outer petals: yellowish white 1A2 yellow at base. Margins of outer petals brown 6D6 and shrivelling. Inner petals: pale yellowish white 2A2, light yellow at base 2A5.

*Underside.*—Yellowish white 1A2.

Length of blooming season in location of production: End of June to beginning of October.

Fragrance: Very slight.

Lasting quality: Good lasts for 14–18 days left on the bush and for cut flowers 13–16 days.

Petals:

*Shape.*—Outside: Generally round with mucronate apex and base. Inside: Oval with mucronate apex and cuneate base.

*Texture.*—Firm

*Number.*—About 90.

*Cleaning.*—Good.

Stamens:

*Number.*—90–100 numerous.

*Anthers.*—Normal, Bright Yellow 3A8.

*Filaments.*—Yellowish 3A5, of irregular heights.

Pistils:

*Number.*—Numerous.

*Stigmas.*—Normal, strew coloured 3B4.

*Styles.*—Greenish 30A5, outer styles have fuchsive top, irregular heights.

Receptable:

*Colour.*—Greyish green 30D6.

*Texture.*—Glabrous, dull.

*Size.*—Length 10 mm × max width 12 mm.

*Shape.*—Goblet shaped in longitudinal section.

General effect of foilage: Medium density, semi-glossy.

*Colour.*—Young foliage: Upperside: 30E7 grass green with reddish brown 8D8 veins, capillaries and margin. Underside: 30D6 leaf green with reddish brown 8D8 veins-particularly pronounced towards margins. Adult foilage: Upperside: 28F 6/7 dark green. Underside: 29E 5/6 greyish green.

The development:

*Vegetation.*—vigorous.

*Blooming.*—Abundant and continual.

*Aptitude to bear fruits.*—None.

*Resistance to frost.*—Good.

*Resistance to disease.*—Good.

I claim:

1. A new and distinct variety of rose plant of the shrub class characterised as to novelty by its fully double flowers of yellowish white with abundant continual blooming and the unusual blend of colouring and shaping of the flower being substantially as shown and described.

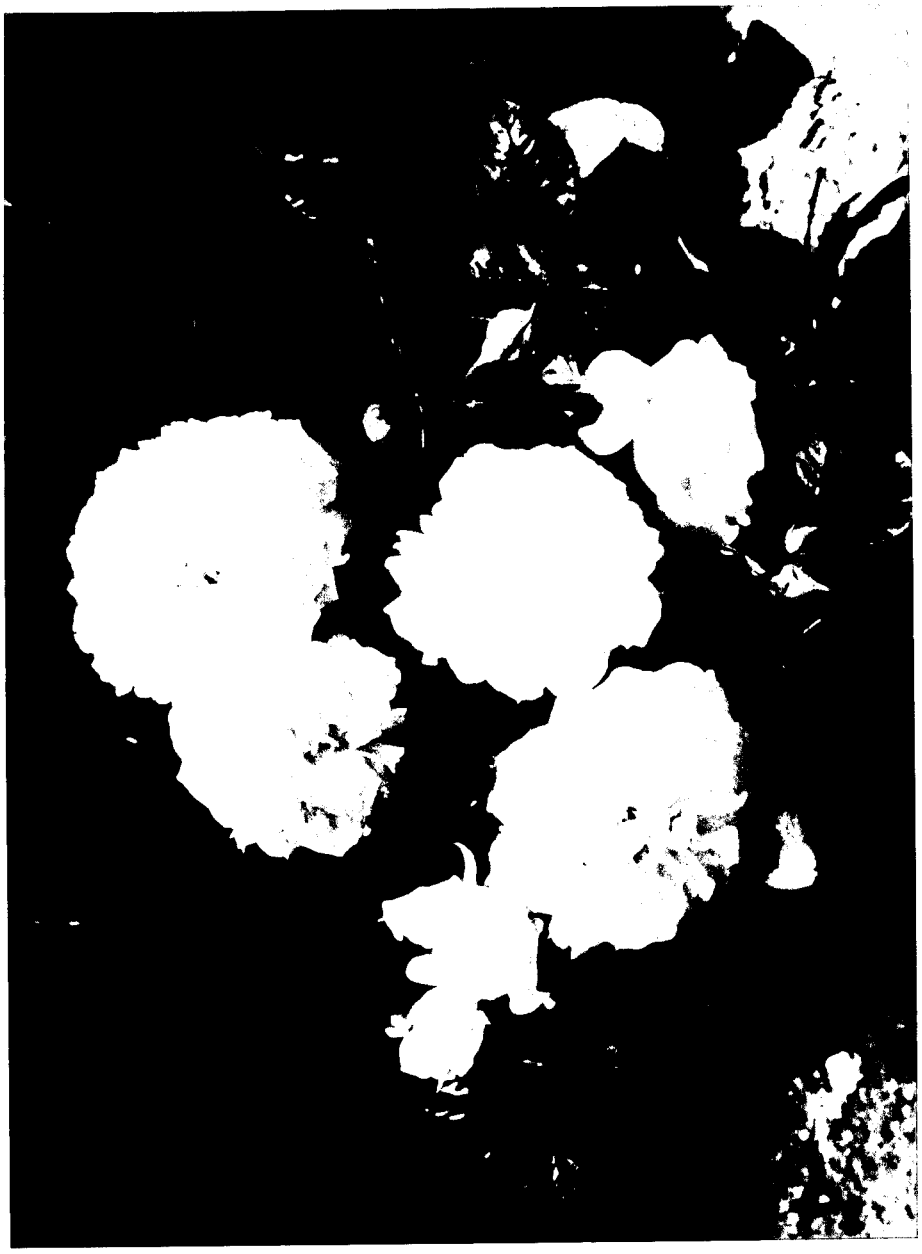

* * * * *